United States Patent
Tatnell et al.

(10) Patent No.: US 10,150,118 B2
(45) Date of Patent: Dec. 11, 2018

(54) CONTROLLED TRANSFER BIOLOGICAL SAMPLE COLLECTION DEVICES AND METHODS OF USING SUCH DEVICES

(71) Applicant: GE Healthcare UK Limited, Buckinghamshire (GB)

(72) Inventors: Peter James Tatnell, Cardiff (GB); Stevan Paul Tortorella, Cardiff (GB); Geraint Seymour, Cardiff (GB); Cheryl Louise Potts, Cardiff (GB); Alan Stuart Pierce, Cardiff (GB); Samantha Jane Ogden, Cardiff (GB); Neil John Williams, Cardiff (GB)

(73) Assignee: GE Healthcare UK Limited, Buckinghamshire (GB)

( * ) Notice: Subject to any disclaimer, the term of this patent is extended or adjusted under 35 U.S.C. 154(b) by 0 days.

(21) Appl. No.: 14/894,682

(22) PCT Filed: May 14, 2014

(86) PCT No.: PCT/EP2014/059894
§ 371 (c)(1),
(2) Date: Nov. 30, 2015

(87) PCT Pub. No.: WO2014/191207
PCT Pub. Date: Dec. 4, 2014

(65) Prior Publication Data
US 2016/0107156 A1    Apr. 21, 2016

(30) Foreign Application Priority Data

May 31, 2013    (GB) .................................... 1309772.0

(51) Int. Cl.
*B01L 3/00*     (2006.01)
*A61B 10/00*    (2006.01)
*G01N 1/10*     (2006.01)
*G01N 1/02*     (2006.01)

(52) U.S. Cl.
CPC .......... *B01L 3/508* (2013.01); *A61B 10/0045* (2013.01); *A61B 10/0096* (2013.01);
(Continued)

(58) Field of Classification Search
CPC ............. B01L 3/5023; B01L 2300/069; B01L 2300/043; G01N 1/02; G01N 2001/028
See application file for complete search history.

(56) References Cited

U.S. PATENT DOCUMENTS 5,063,791 A    11/1991 Martin
5,308,580 A    5/1994 Clark
(Continued)

FOREIGN PATENT DOCUMENTS

| WO | 9718036 A1 | 5/1997 |
| WO | 2012163788 A1 | 12/2012 |
| WO | 2013064558 A1 | 5/2013 |

OTHER PUBLICATIONS

Great Britain Search Report and Written Opinion dated Nov. 29, 2013 which was issued in connection with Great Britain Patent Application No. 1309772.0 which was filed on May 31, 2013.
(Continued)

*Primary Examiner* — Sally A Merkling
(74) *Attorney, Agent, or Firm* — Evershed Sutherland (US) LLP

(57) ABSTRACT

A controlled transfer biological sample material collection device is disclosed which includes a body and a sample collection member for collecting the biological sample material, the body housing a sample storage medium for generally dry storage of the biological material, the collection member being moveable from an exposed position where collection of a biological sample is possible, to a transfer position which effects transfer of at least a portion of the collected sample to said medium. The body of the
(Continued)

device slideably supports the sample collection member, and the body or collection member includes a ramp-like projection portion operable to force the collection member into the transfer position against the medium and to effect the transfer as the collection member slides within the body.

16 Claims, 6 Drawing Sheets

(52) U.S. Cl.
CPC ........... *B01L 3/5023* (2013.01); *B01L 3/5029* (2013.01); *G01N 1/10* (2013.01); *B01L 2300/0609* (2013.01); *B01L 2300/069* (2013.01); *B01L 2300/0809* (2013.01); *B01L 2300/0825* (2013.01); *B01L 2300/0848* (2013.01); *G01N 2001/028* (2013.01)

(56) References Cited

U.S. PATENT DOCUMENTS

| | | | |
|---|---|---|---|
| 6,241,689 B1 * | 6/2001 | Chard | B01L 3/5023 600/584 |
| 6,372,516 B1 * | 4/2002 | Sun | B01L 3/5023 422/408 |
| 7,294,502 B2 | 11/2007 | Eckermann et al. | |
| 7,748,283 B2 | 7/2010 | Harvey et al. | |
| 9,370,775 B2 | 6/2016 | Harvey et al. | |
| 2004/0126281 A1 | 7/2004 | Morrison | |
| 2004/0161855 A1 | 8/2004 | Kvasnik et al. | |
| 2005/0036916 A1 | 2/2005 | Thomas et al. | |
| 2006/0246598 A1 | 11/2006 | Dai et al. | |
| 2008/0196517 A1 * | 8/2008 | Harvey | B01L 3/5023 73/864.91 |

OTHER PUBLICATIONS

International Search Report dated Aug. 12, 2014 which was issued in connection with PCT Patent No. EP2014/059894 which was filed on May 14, 2014.
Chinese Office Action for CN Application No. 201480031304.2 dated Sep. 12, 2016 (16 pages).
Japanese Office Action for JP Application No. 2016-515707 dated Feb. 27, 2018 (4 pages).

* cited by examiner

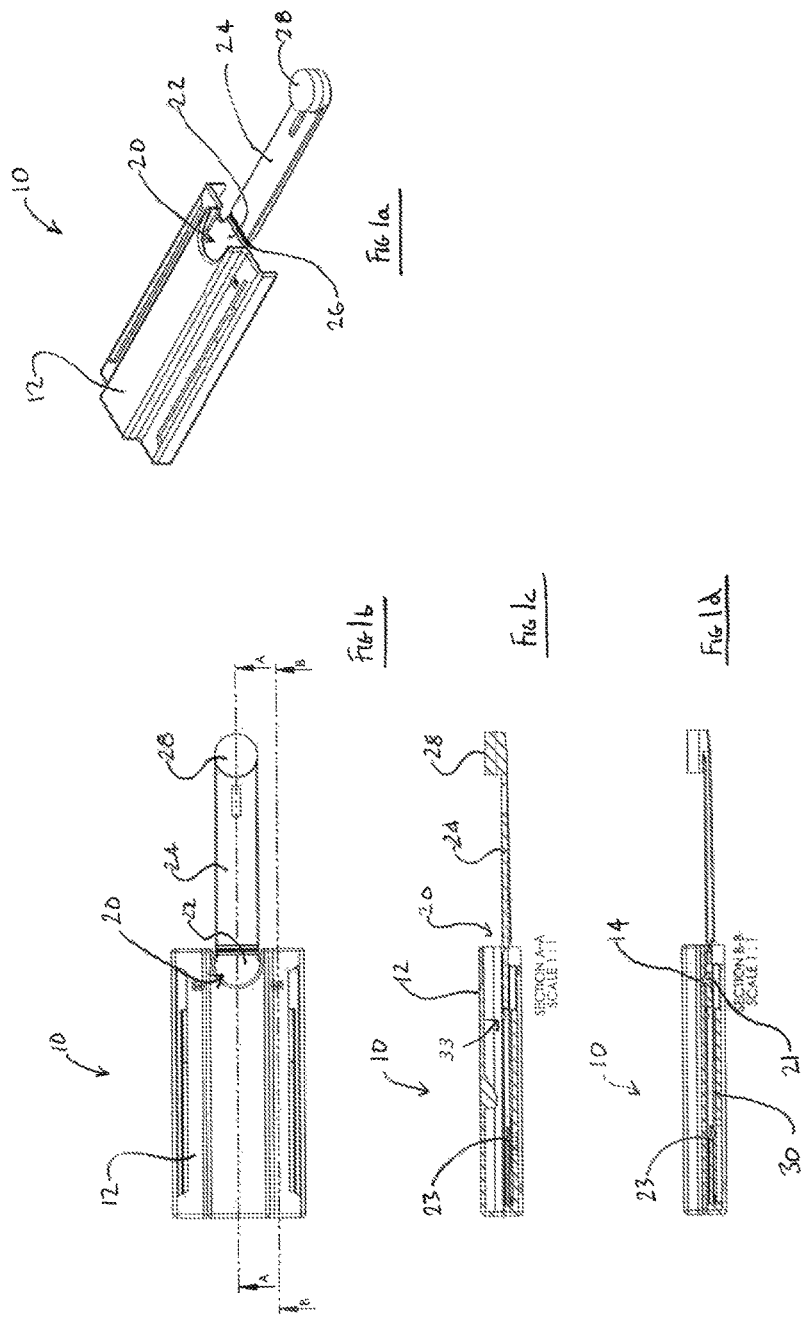

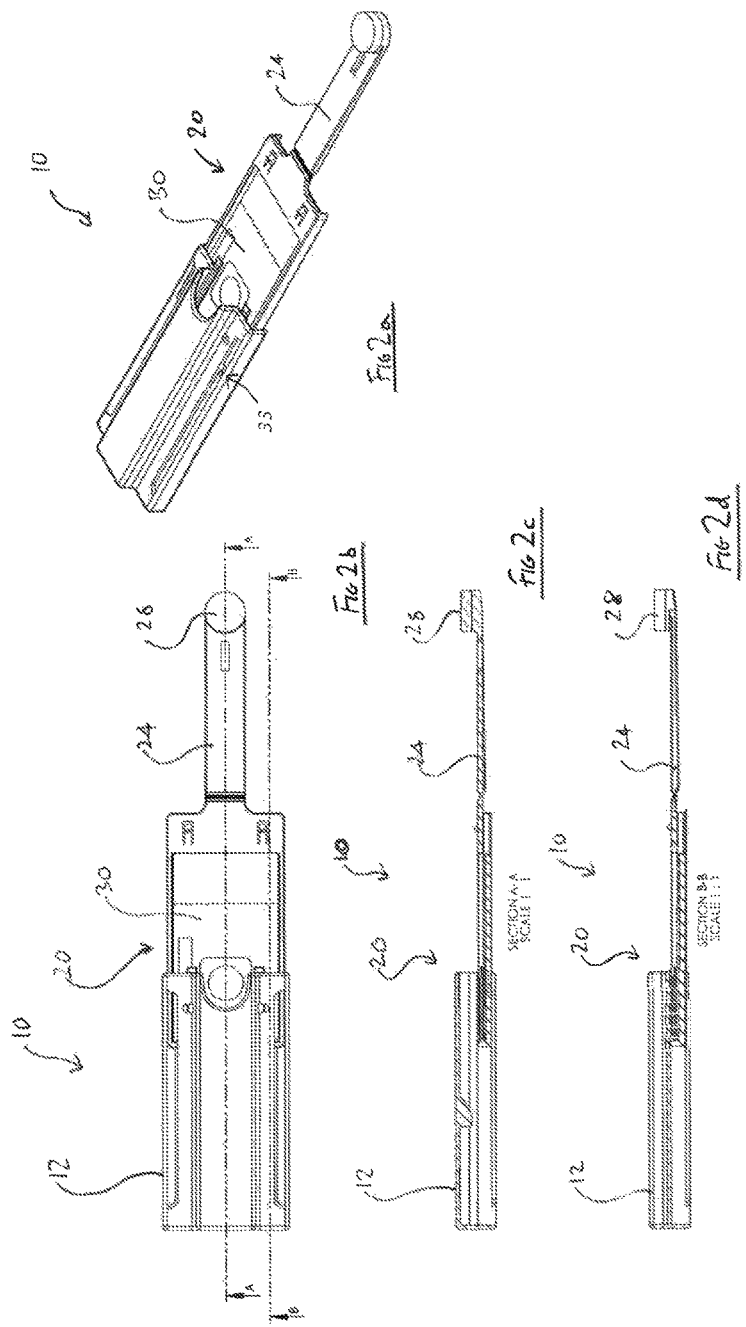

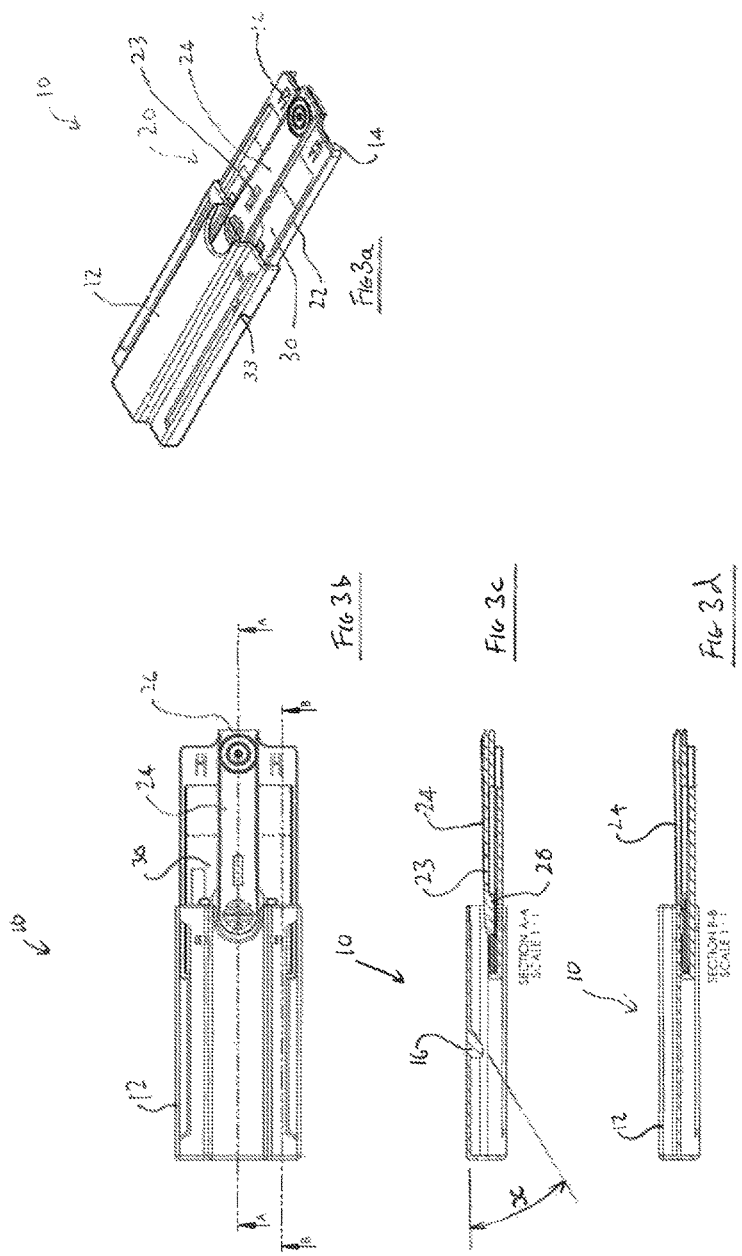

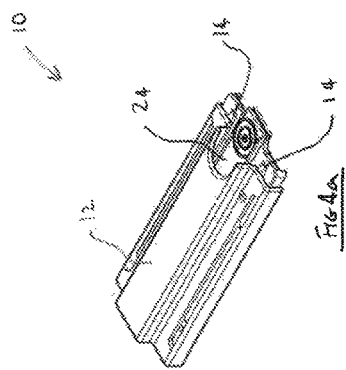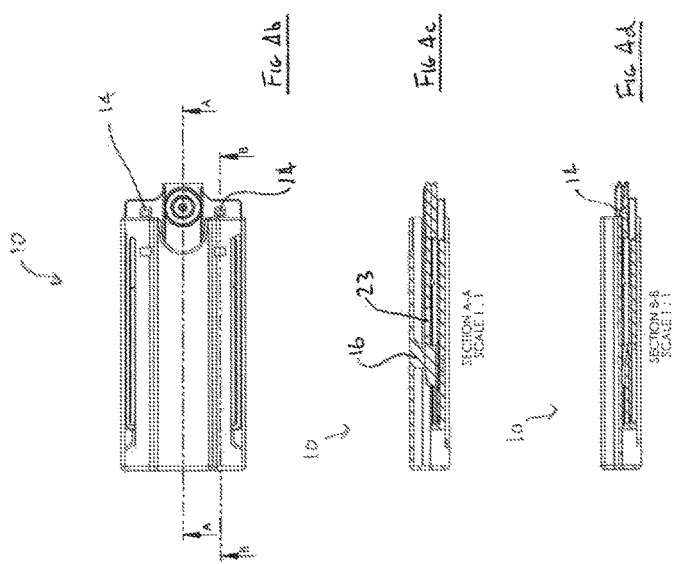

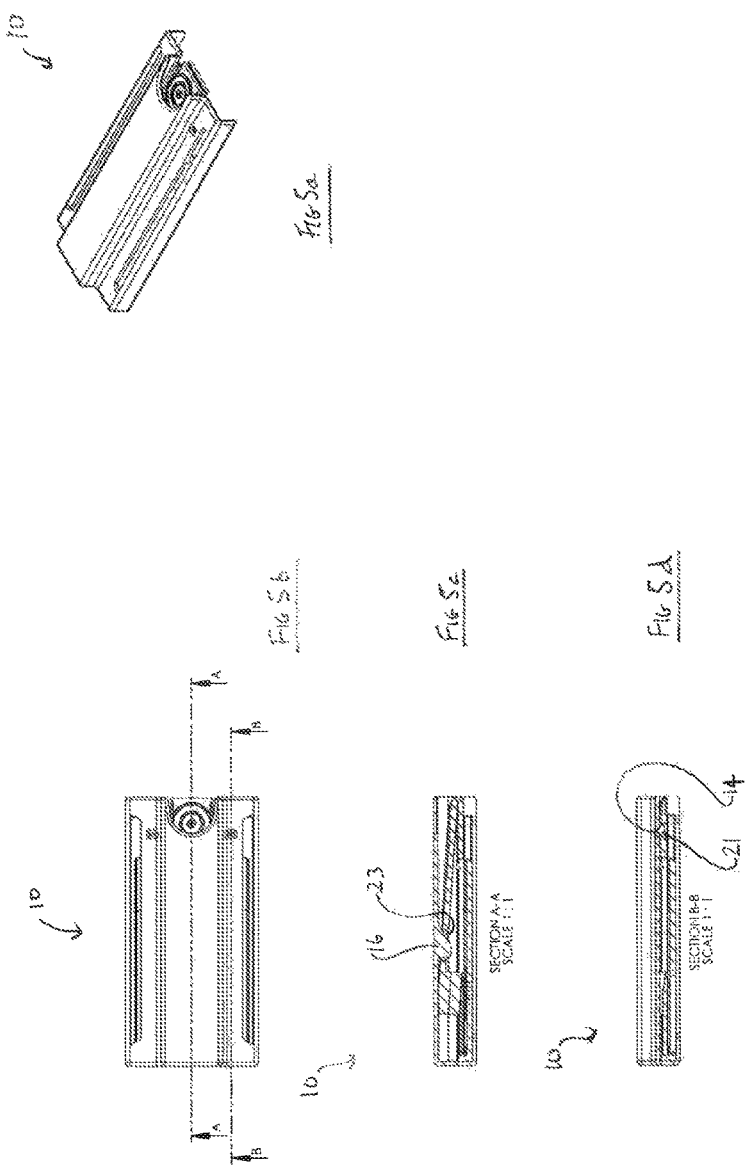

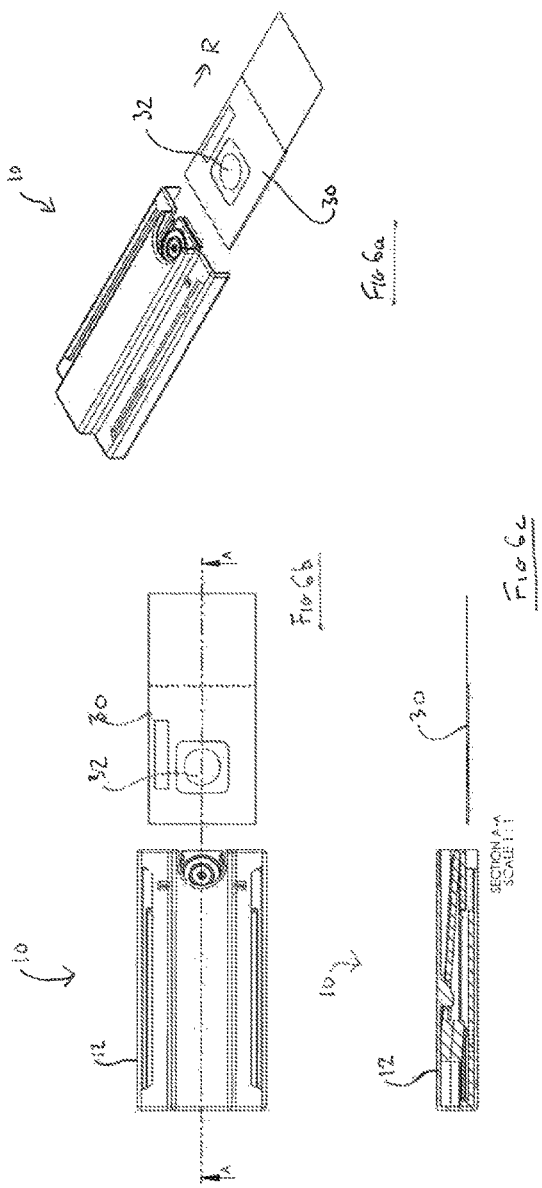

CONTROLLED TRANSFER BIOLOGICAL SAMPLE COLLECTION DEVICES AND METHODS OF USING SUCH DEVICES

BACKGROUND OF THE INVENTION

Field of the Invention

The field of the present invention relates to a controlled transfer biological collection device using a dry solid transfer and storage medium, and a method for the collection of biological material of interest, for example genetic or proteinaceous material, in a form suitable for temporary or long term storage, and/or subsequent analysis. Specifically, the present invention provides for a sampling device that controls the transfer of the biological sample to the storage medium by holding the storage medium and a moveable sample collection member having an analyte collection surface.

Description of the Related Art

The collection of biological samples (such as blood) and extracting DNA for genetic analysis from the sample has been widely used by the forensics and medical community for identification purposes, for paternity testing, for genetic diagnostic testing in new born screening programs, for genetic typing for predisposition to disease and for genetic characterisation for drug susceptibility. However, due to the invasive nature of blood collection, alternative non-invasive methods are coming into favour. Current methods involve scraping cellular mucosa from inside the oral cavity using any of a number of different devices such as cytobrushes, cotton or artificial fibre swabs, mouthwash swish and rinse methods, foam tipped swabs, and supported cellulosic filter paper collection techniques (known as the Bode method). These methods require time-consuming, labour intensive extraction methods.

The introduction of treated storage media into the forensics community has significantly streamlined the collection and extraction of DNA from a variety of samples. One such treated medium is available commercially under the brand name FTA® from Whatman, Inc. and is described in one or more of the following patents U.S. Pat. No. 6,627,226, U.S. Pat. No. 6,447,804, U.S. Pat. No. 6,294,203, U.S. Pat. No. 6,168,922, U.S. Pat. No. 5,976,572, U.S. Pat. No. 5,972,386, U.S. Pat. No. 5,939,259, and U.S. Pat. No. 5,756,126. The medium is used with a plastics collecting device known as Easicollect® from Whatman Inc, and described in US20100106057 (Harvey et al). This known collecting device includes an arm having buccal cell collector foam pad at one end, which arm is manipulated to collect buccal cells, and is further manipulated to pivot, and thereby to transfer those cells from the foam pad onto an FTA medium held at an opposing end of the device.

Whilst this technique is adequate, the transfer buccal cells to the treated medium in a consistent and reproducible manner remains a matter of operator skill, which is not ideal particularly where operators may seldom use the device. The correct pressure and timing of the transfer step are important, and it is essential that the exposed medium is not contaminated while transfer takes place.

Improvements in the device design were disclosed in WO2012/163788 (GE Healthcare), however, the inventors have realised that yet further improvements in the ease of use and prevention of contamination are possible.

BRIEF SUMMARY OF THE INVENTION

The present invention relates to a controlled transfer biological collection device using a dry solid storage and transfer medium and a method for the collection of biological material of interest—a sample (which may be genetic or proteinaceous material) in a form suitable for storage and/or subsequent analysis.

According to a first aspect, the invention provides a controlled transfer biological sample material collection device, comprising: a body slideably supporting a sample collection member for collecting the biological sample material of interest, the body housing a treated medium for dry storage of the biological material, the collection member being moveable from an exposed position where collection of a biological sample is possible, to a transfer position which effects transfer of at least a portion of the collected sample to the medium, the device being characterised in that the housing includes a ramp portion operable to force the collection member into the transfer position against the medium and to effect said transfer as the collection member slides within the housing.

In an embodiment, the collection member includes a portion slideable within the housing which slideable portion carries the medium.

In an embodiment, the collection member further includes an arm hinged to the slideable portion, which arm carries a resilient pad for sample collection, wherein the slideable portion and the arm are foldable together to slide within the body and together to slide across said ramp to effect the transfer.

In an embodiment the arm includes a slot, which slot accepts the ramp thereby to separate the medium and the pad following the transfer.

In an embodiment the slideable portion and medium are positionable within the body so as to be substantially enclosed by the body, and when in that position, the arm is able to adopt said exposed position, and the slideable portion and medium are further positionable so as to be partially within the body but able to adopt said folded together position with the arm, for collective reinsertion into the body and to effect said transfer.

In an embodiment, the extent of movement of the slideable portion is limited by stops on or in the body.

In an embodiment, the medium is removable from the slideable portion, following said transfer.

The invention is further characterised by the claims.

BRIEF DESCRIPTION OF THE DRAWINGS

FIG. 1a is a perspective view of a preferred embodiment of the present invention showing the claimed device in an initial position;

FIG. 1b is a plan view of the device shown in FIG. 1;

FIGS. 1c and 1d are sections through the device shown in FIG. 1b;

FIGS. 2a through to FIG. 6d are further views of the device of FIG. 1a, in different positions.

DETAILED DESCRIPTION OF THE INVENTION

A preferred embodiment is shown in FIG. 1a. A collection device (10) for a biological sample that contains degradable biologically sourced analytes is shown which comprises a body 12 which slideably holds a collection member 20. The collection member has a sample storage portion in the form of a tray 22 for supporting a sample storage medium 30. Examples of a storage medium material a suitable for the present invention include untreated filter paper, such as #903® brand paper (Whatman, Inc., Florham Park, N.J.

USA) or treated filter papers, such as FTA and FTA Elute brand paper (also from Whatman, Inc., Florham Park, N.J. USA). These treated media are described in US patents referenced above. Such treated media provide a simple safe method for collection, shipping and storage of biological samples. They also contain chemistries which make it easy to isolate DNA from complex samples such as blood. Samples collected on treated or untreated media are dried for storage and can be stored at room temperature for long periods of time.

The collection member 20 further includes an arm 24 hinged to the sample storage portion by means of a hinge 26 formed from flexible moulded plastics. At the distal end of arm 24 a resilient pad 28 of foamed polymeric material is fixed to the arm, which acts as a sample collector when required.

In the position shown in FIGS. 1a and 1b, the device is ready to be used to collect a biological sample by wiping the pad 28, or otherwise making contact, over an area of interest, for example to collect buccal cells from the inner cheek surface of the mouth of a subject.

FIG. 1b shows the device 10 in plan view. FIG. 1c shows the device 10 in section along line A-A in FIG. 1b, and FIG. 1d shows the device in section along line B-B. As can be seen in more detail in FIGS. 1c and 1d, the tray 22 holds a storage medium 30, and the 22 is slideable in the body 12 along with the medium 30 and the arm 24. However, the tray is held resiliently in position by means of detents 21 formed on the tray 22 which cooperate with apertures 14 in the body 12.

Once the sample has been collected, the collection member 20 is drawn out of the body 12 as shown in FIG. 2a, until the tray abuts further stop members 33. Further details are shown in FIGS. 2b, 2c and 2d. In that position, the medium 30 becomes exposed.

The arm 24 is then folded over toward the medium 30 as illustrated in FIGS. 3a,3b,3c and 3d. In this position, the pad 28 may lightly touch the medium 30 to transfer some biological sample material to the medium but that is not certain. It will be noted that the arm 24 includes a through-slot 23, the function of which is described in more detail below.

The user then pushes the collection member 30 back into the body 12 holding the arm folded, as shown in FIG. 4a. The user will feel resistance as the detents 14 abut the edge of the body 12. At this point a ramp 16 on the body 12 forces the back of the arm 24, adjacent the pad 28, toward the medium 28 to provide a repeatable and constant contact force, and thereby a controlled transfer of biological material onto the medium 30 is obtained.

The user pauses with the device 10 in this position for a predetermined time. It has been found that force is a more accurate predictor of material transference rather than time so the pause time is not critical, but 5 to 15 seconds has proven successful, more preferably about 10 seconds.

The user then pushes the tray 22 fully into the body 12, until the pad lifts off the medium 30. This lifting occurs when the through slot 23 coincides with the ramp 16 so the through slot surrounds the ramp 16. This position is shown in FIGS. 5a,5b,5c, and 5d. In this position the complementary features 14 and 21 once again come into alignment. The user can then either remove the medium 30 as shown in FIGS. 6a,6b and 6c, for storage, or transportation to a laboratory for storage or further processing, or may do the same with the whole device still containing the medium 30.

Since the medium may contain at least one stabilizing reagent the sample will then be preserved for transport or storage. Suitable such reagents include either the combination of a weak base, a chelating agent, and, optionally, uric acid or a urate salt or simply the addition of a chaotropic salt, alone or in combination with a surfactant. The "weak base" of the composition may be a Lewis base which has a pH of about 6 to 10, preferably about pH 8 to 9.5. One function of the weak base is to act as a buffer to maintain a composition pH of about 6 to 10, preferably about pH 8.0 to 9.5, for example, pH 8.6. Hence, a weak base suitable for the composition of the invention may, in conjunction with other components of the composition, provide a composition pH of 6 to 10, preferably, about pH 8.0 to 9.5. Suitable weak bases according to the invention include organic and inorganic bases. Suitable inorganic weak bases include, for example, an alkali metal carbonate, bicarbonate, phosphate or borate (e.g., sodium, lithium, or potassium carbonate). Suitable organic weak bases include, for example, tris-hydroxymethyl amino methane (Tris), ethanolamine, triethanolamine and glycine and alkaline salts of organic acids (e.g., trisodium citrate). A preferred organic weak base is a weak monovalent organic base, for example, Tris. The Tris may be either a free base or a salt, for example, a carbonate salt.

A preferred chelating agent is a strong chelating agent. By "strong" chelating agent it is meant that the agent binds multivalent metal ions with a comparable or better affinity than ethylene diamine tetraacetic acid (EDTA). A preferred chelating agent according to the invention is EDTA.

Anioinic surfactants are examples of surfactants which are useful in the present invention. A preferred anionic detergent is a strong anionic detergent. As used herein, a "strong" anionic detergent includes a hydrocarbon moiety, aliphatic or aromatic, containing one or more anionic groups. Particularly preferred anionic detergents suitable for the invention include sodium dodecyl sulphate (SDS) and sodium lauryl sarcosinate (SLS). In a preferred embodiment, the anionic detergent causes inactivation of most microorganisms which have protein or lipids in their outer membranes or capsids, for example, fungi, bacteria or viruses. This includes microorganisms which may be pathogenic to humans and are present in a biological sample. Also preferably, the storage medium will have a visual delineation (32 FIG. 6a) placed around the transfer area of the storage medium such that if removed from the tray 22 a user will know where the material was deposited without reference to the device.

The present device 10 can be used to collect samples such as degradable biologically sourced analytes such as nucleic acids, proteins, and respective fragments thereof. The biological sample can be selected from the group consisting of saliva, blood, serum, lymph fluids, buccal cells, mucosal cells, cerebrospinal fluid, semen, vaginal fluid, faeces, plasma, urine, a suspension of cells, or a suspension of cells and viruses.

Preferably, the present device is dimensioned and configured such that tray 22 releasably holds the storage medium 30 by holding means 23 in the form of resilient tabs. Thus, one can separate the medium 30 from the remainder of the device 10 for subsequent processing or storage. The tension on the tabs 23 allows for manual or automated extraction, but does not allow for accidental loss of the medium 30.

If used in buccal cell collection, the pad 28 should be dimensioned and configured to fit within the human mouth. For record keeping and traceability the present device should also comprise an identification label (such as conventional bar coding) on not only the medium 30, but also the body 12. RFID tags may be employed for this purpose.

To ensure device integrity, the present device can also comprise a sterility envelope surrounding the other device elements. Preferably, those other elements are sterile and free from any biological sample analytes (made for example, from medical grade plastics), which can be done through conventional techniques such as irradiation after the envelope is sealed.

Kits can be made that incorporate the above device along with any combination of associated equipment or reagents including purification reagents, buffers, or the like and storage systems, containers, or the like. In this regard, the present invention further provides a kit comprising a device as defined herein and one or more components selected from the group consisting of purification reagents for subsequent analysis of the sample, buffers, storage systems and containers.

Example of Device Use:

The present device can be used for biological sample collection for the following purposes: the collection of buccal cell samples for criminal databases; the collection of crime scene samples (i.e., rehydrated blood, semen, saliva and liquid samples of the same); the collection of sexual assault samples; the collection of buccal samples for population genetics or pharmacogenomics studies; the collection of buccal samples for personal genetic ID archiving; the collection of bacterial or parasite samples from food sources; the collection of blood from meat at slaughterhouse for meat traceability; or the collection of biological samples from animals for veterinary diagnostics.

Although one embodiment only has been illustrated, it will be apparent to the skilled addressee that modifications, variants, additions and omissions are possible within the scope and spirit of the invention defined herein.

For example, a ramp 16 has been described and illustrated, but any ramp-like projection could be used, i.e. a projection which forms an acute angle between the direction of sliding of the collection member 20 and the surface of the ramp or projection. The acute angle is preferably about 30 degrees as illustrated by the angle x in FIG. 3c. The ramp has been shown on the body 12, but an equally effective arrangement would be to mount the ramp on the arm 24, and have a reaction surface on the body. Sliding the arm beyond the reaction surface could release the arm from the transfer position in the same way that the slot 23 releases the arm. 'Sliding and similar terms mean linear or substantially linear movement.

Moulded plastics is the preferred material for the body 12 and collection member 20, but other materials could be employed, for example metals, for example diecast aluminium alloy.

What is claimed is:

1. A controlled transfer biological sample material collection device, comprising:
    a body; and
    a sample collection member for collecting the biological sample material, the body housing a sample storage medium for generally dry storage of the biological sample material, the collection member being moveable from an exposed position where collection of the biological sample material is possible to a transfer position which effects transfer of at least a portion of the collected biological sample material to said medium, wherein the body slideably supports the sample collection member, wherein the body or collection member includes a ramp operable to force the collection member into the transfer position against the medium and to effect said transfer as the collection member slides within the body, and wherein the body and the collection member include complementary stop features arranged to stop sliding movement of the collection member when fully extended at the exposed position to prevent the collection member from separating completely from the body when the collection member slides away from the body to assume the exposed position.

2. A device as claimed in claim 1, wherein the collection member includes a slideable portion that is slideable within the housing, and wherein the slideable portion carries the medium.

3. A device as claimed in claim 2, wherein the collection member further comprises an arm hinged to the slideable portion, wherein the arm carries a resilient pad for sample collection, and wherein the slideable portion and the arm are foldable together to provide a folded-together position, to slide within the body to effect the transfer under the influence of the ramp.

4. A device as claimed in claim 3, wherein the ramp is formed on the body, and the arm includes a slot, and wherein the slot accepts the ramp thereby to separate the medium and the pad following the transfer.

5. A device as claimed in claim 3, wherein the slideable portion and medium are configured to be positioned within the body so as to be substantially enclosed by the body, and when in that position, the arm is not able to adopt said exposed position, and the slideable portion and medium are further configured to be positioned so as to be only partially within the body but able to adopt said folded-together position with the arm, for collective reinsertion into the body and to effect said transfer.

6. A device as claimed in claim 2, wherein the slideable portion comprises some of the complementary stop features, and wherein the extent of movement of the slideable portion is limited by the complementary stop features on the body and on the slideable portion.

7. A device as claimed in claim 2, wherein the medium is removable from the slideable portion.

8. A method for controlled transfer biological sample material collection, the method comprising:
    providing a device, comprising a body and a sample collection member for collecting the biological sample material, the body housing a sample storage medium for generally dry storage of the biological sample material,
    exposing the collection member and collecting the biological sample material on the collection member;
    moving the collection member from an exposed position wherein collection of the biological sample material is possible, to a transfer position which effects transfer of at least a portion of the collected biological sample material to said medium, and
    sliding the collection member relative to the body to said transfer position, wherein a ramp on the body or the collection member forces the collection member against the medium, and
    wherein the body and the collection member include complementary stop features arranged to stop sliding movement of the collected member when fully extended at the exposed position to prevent the collection member from separating completely from the body when the collection member slides away from the body to assume the exposed position.

9. A device as claimed in claim 4, wherein the slideable portion and medium are configured to be positioned within the body so as to be substantially enclosed by the body, and when in that position, the arm is not able to adopt said exposed position, and the slideable portion and medium are further configured to be positioned so as to be only partially within the body but able to adopt said folded-together position with the arm, for collective reinsertion into the body and to effect said transfer.

10. A device as claimed in claim 3, wherein the slideable portion comprises some of the complementary stop features, and wherein the extent of movement of the slideable portion is limited by the complementary stop features on the body and on the slideable portion.

11. A device as claimed in claim 4, wherein the slideable portion comprises some of the complementary stop features, and wherein the extent of movement of the slideable portion is limited by the complementary stop features on the body and on the slideable portion.

12. A device as claimed in claim 5, wherein the slideable portion comprises some of the complementary stop features, and wherein the extent of movement of the slideable portion is limited by the complementary stop features on the body and on the slideable portion.

13. A device as claimed in claim 3, wherein the medium is removable from the slideable portion.

14. A device as claimed in claim 4, wherein the medium is removable from the slideable portion.

15. A device as claimed in claim 5, wherein the medium is removable from the slideable portion.

16. A device as claimed in claim 6, wherein the medium is removable from the slideable portion.

* * * * *